(12) United States Patent
Barneoud et al.

(10) Patent No.: US 9,789,102 B2
(45) Date of Patent: Oct. 17, 2017

(54) H3 RECEPTOR ANTAGONIST FOR USE IN THE TREATMENT OF ALZHEIMER'S DISEASE

(71) Applicant: SANOFI, Paris (FR)

(72) Inventors: Pascal Barneoud, Paris (FR); Veronique Blanchard-Bregeon, Paris (FR); Veronique Mary, Evry (FR); Jean Menager, Chilly Mazarin (FR); Philippe Delay-Goyet, Paris (FR); Mathilde Lopez-Grancha, Massy (FR); Thomas Rooney, Orsay (FR); Nathalie Schussler, Fontenay aux Roses (FR)

(73) Assignee: SANOFI, Paris (FR)

(*) Notice: Subject to any disclaimer, the term of this patent is extended or adjusted under 35 U.S.C. 154(b) by 0 days.

(21) Appl. No.: 14/872,812

(22) Filed: Oct. 1, 2015

(65) Prior Publication Data

US 2016/0101099 A1 Apr. 14, 2016

Related U.S. Application Data (63) Continuation of application No. 14/506,089, filed on Oct. 13, 2014, now abandoned, which is a continuation of application No. PCT/EP2013/057241, filed on Apr. 5, 2013.

(60) Provisional application No. 61/792,635, filed on Mar. 15, 2013.

(30) Foreign Application Priority Data

Apr. 6, 2012 (EP) .................................... 12305415

(51) Int. Cl.
C07D 401/02 (2006.01)
A61K 31/4725 (2006.01)

(52) U.S. Cl.
CPC .............................. *A61K 31/4725* (2013.01)

(58) Field of Classification Search
None
See application file for complete search history.

(56) References Cited

U.S. PATENT DOCUMENTS

| | | |
|---|---|---|
| 7,446,103 B2 | 11/2008 | Best et al. |
| 7,592,347 B2 | 9/2009 | Bruton et al. |
| 7,638,631 B2 | 12/2009 | Bruton et al. |
| 7,678,807 B2 | 3/2010 | Diaz Martin et al. |
| 7,799,773 B2 | 9/2010 | Bamford et al. |
| 7,833,999 B2 | 11/2010 | Diaz Martin et al. |
| 7,846,922 B2 | 12/2010 | Bruton et al. |
| 7,888,347 B2 | 2/2011 | Bamford et al. |
| 8,273,733 B2 | 9/2012 | Diaz Martin et al. |
| 8,524,700 B2 | 9/2013 | Diaz Martin et al. |
| 8,664,245 B2 | 3/2014 | Langevin et al. |
| 2005/0031651 A1 | 2/2005 | Gervais et al. |
| 2006/0052597 A1 | 3/2006 | Best et al. |
| 2006/0247227 A1 | 11/2006 | Bailey et al. |
| 2006/0293298 A1 | 12/2006 | Bamford et al. |
| 2007/0054917 A1 | 3/2007 | Bruton et al. |
| 2007/0060566 A1 | 3/2007 | Bailey et al. |
| 2007/0105834 A1 | 5/2007 | Diaz Martin et al. |
| 2007/0208005 A1 | 9/2007 | Parr et al. |
| 2007/0232590 A1 | 10/2007 | Bamford et al. |
| 2008/0009479 A1 | 1/2008 | Heightman et al. |
| 2008/0045506 A1 | 2/2008 | Bruton et al. |
| 2008/0161289 A1 | 7/2008 | Baily et al. |
| 2009/0306052 A1 | 12/2009 | Wilson |
| 2010/0204242 A1 | 8/2010 | Best et al. |
| 2011/0020447 A1 | 1/2011 | Clarke et al. |
| 2011/0028475 A1 | 2/2011 | Diaz Martin et al. |
| 2011/0184000 A1 | 7/2011 | Giovannini et al. |
| 2011/0189280 A1 | 8/2011 | Clarke et al. |
| 2011/0212960 A1 | 9/2011 | Heine et al. |
| 2012/0149728 A1 | 6/2012 | Langevin et al. |
| 2015/0031893 A1 | 1/2015 | Barneoud et al. |

FOREIGN PATENT DOCUMENTS

| | | |
|---|---|---|
| EP | 2647377 | 10/2013 |
| EP | 2745876 | 6/2014 |
| RU | 2378257 C2 | 4/2008 |
| WO | WO 02/076925 | 10/2002 |
| WO | WO 2005/118547 | 12/2005 |
| WO | WO 2005/118548 A1 | 12/2005 |
| WO | WO 2007/147883 | 12/2007 |
| WO | WO 2010/151611 | 12/2010 |
| WO | WO 2011/051423 | 5/2011 |
| WO | WO 2012/168664 | 12/2012 |

OTHER PUBLICATIONS

Anderson et al, Brain (2008) ,vol. 131, pp. 1736-1748.*
International Search Report for WO2013/150150 dated Oct. 10, 2013.
Bitner, et al., In-Vivo Histamine H3 Receptor Antagonism Activates Cellular Signaling Suggestive of Symptomatic and Disease Modifying Efficacy in Alzheimer's Disease, Neuropharmacology, vol. 60, (2011), pp. 460-466.
Brioni, et al., Discovery of Histamine H3 Antagonists for the Treatment of Cognitive Disorders and Alzheimer's Disease, The Journal of Pharmacology and Experimental Therapeutics, vol. 336, No. 1, pp. 38-46, (2011).
Schindowski, et al., Alzheimer's Disease-Like Tau Neuropathology Leads to Memory Deficits and Loss of Functional Synapses in a Novel Mutated Tau Transgenic Mouse Without Any Motor Deficits, The American Journal of Pathology, vol. 169, No. 2, (2006), pp. 599-616.
Sun, et al., Comparative Analysis of an Improved Thioflavin-S Stain, Gallyas Silver Stain, and Immunohistochemistry for Neurofibrillary Tangle Demonstration of the Same Sections, The Journal of Histochemistry & Cytochemistry, vol. 50, No. 4, pp. 463-472, (2002).
Goedert, et al., Monoclonal Antibody AT8 Recognises Tau Protein Phosphorylated at Both Serine 202 and Threonine 205, Neuroscience Letters, vol. 189, (1995), pp. 167-170.

(Continued)

*Primary Examiner* — Zinna Northington Davis
(74) *Attorney, Agent, or Firm* — Hoxie & Associates LLC (57) ABSTRACT

This disclosure relates to methods of using 2-(cyclohexylmethyl)-N-{2-[(2S)-1-methylpyrrolidin-2-yl]ethyl}-1,2,3,4-tetrahydroisoquinoline-7-sulfonamide in a disease modifying therapy of Alzheimer's disease, other tauopathies and related neurodegenerative diseases.

19 Claims, 4 Drawing Sheets

(56) References Cited

OTHER PUBLICATIONS

Bongers, et al., The Akt/GSK-3β Axis as a New Signaling Pathway of the Histamine H3 Receptor, Journal of Neurochemistry, (2007), vol. 103, pp. 248-258.
Markosyan, et al., H3 Receptor Antagonism Activates Cellular Signaling Suggestive of Symptomatic and Disease Modifying Efficacy in Alzheimer's Disease, Presentation abstract from Neuroscience 2009, (Oct. 21, 2009).
Stemmelin, The Histamine H3 Receptor Antagonist SAR110894D Prevents the Development of Tau Neurofibrillary Tangles and Improves Cognitive Deficits in a Mouse Model of Tauopathy, Presentation abstract from Neuroscience 2013, (Nov. 12, 2013).
Griebel, et al., Awakening Properties of Newly Discovered Highly Selective H3 Receptor Antagonists in Rats, Behavioural Brain Research, vol. 232, (2012), pp. 416-420.
Griebel, et al., SAR110894, A Potent Histamine H3-Receptor Antagonist, Display Procognitive Effects in Rodents, Pharmacology, Biochemistry and Behavior, vol. 102, (2012), pp. 203-214.
Braak, et al., Demonstration of Amyloid Deposits and Neurofibrillary Changes in Whole Brain Sections, Brain Pathology, vol. 1, pp. 213-216, (1991).
Giovannini, et al., Effects of Histamine H3 Receptor Agonists and Antagonists on Cognitive Performance and Scopolamine-Induced Amnesia, Behavioural Brain Research, vol. 104, (1999), pp. 147-155.
Korte, et al., Characterization and Tissue Distribution of H3 Histamine Receptors in Guinea Pigs by Na-Methylhistamine, Biochemical and BioPhysical Research Communications, pp. 979-986, vol. 168, No. 3, (1990).
Liu, et al., Does the [3H]Mepyramine Binding Site Represent the Histamine H1 Receptor? Re-Examination of the Histamine H1 Receptor WIth Quinine, The Journal of Pharmacology and Experimental Therapeutics, vol. 268, No. 2, pp. 959-964, (1994).
Lovenberg, et al., Cloning of Rat Histamine H3 Receptor Reveals Distinct Species Pharmacological Profiles, The Journal of Pharmacology and Experimental Therapeutics, vol. 293, No. 3, pp. 771-778, (2000).
Tozer, et al., Histamine H3 Receptor Antagonists, Exp. Opin. Ther. Patents, (2000), vol. 10, No. 7, pp. 1045-1055.
West, et al., Identification of Two H3-Histamine Receptor Subtypes, Molecular Pharmacology, vol. 38, pp. 610-613, (1990).
Black et al., SAR110894, A Novel, Potent and Selective H3-Receptor (H3-R) Antagonist: III. Potential Activity in Positive Symptom and Cognitive Domains of Schizophrenia Using Latent Inhibition (LI) Models in the Rat, Poster 160.19/FF4, presented at the 38th, Annual Meeting Society for Neuroscience (2008) (1 page).

Cho, et at., Additive Effects of a Cholinesterase Inhibitor and a Histamine Inverse Agonist on Scopolamine Deficits in Humans, Psychopharmacology, (2011), vol. 218, pp. 513-524.
Delay-Goyet, Phillipe et al. "SAR110894, a potent histamine H3-receptor antagonist, displays disease-modifying activity in a transgenic mouse model of tauopathy" Published by Elsevier Inc. on behalf of the Alzheimer's Association, Alzheimer's & Dementia: Translational Research & Clinical Interventions 2 (2016) 267-280.
Guillot, et at, SAR110894, A Novel, Potent and Selective H3-Receptor (H3-R) Antagonist: I. Binding and Functional Characterization, (2008), pp. 1-4, Presentation Abstract from Neuroscience 2008.
Guillot, et al., SAR110894, A Novel, Potent and Selective H3-Receptor (H3-R) Antagonist: I. Binding and Functional Characterization Poster 160.21/FF6, presented at the 38th Annual Meeting Society for Neuroscience (2008) (1 page).
Huang et al., "Searching for the Multi-Target-Directed Ligands against Alzheimer's Disease: Discovery of quinoxaline-based hybrid compounds with AChE, $H_3R$ and BACE 1 inhibitory activities", Bioorg. Med. Chem. 19, 2011 7158-7167.
Pichat, et al, SAR110894, A Novel, Potent and Selective H3-Receptor (H3-R) Antagonist II. Effects in Models Predictive of Therapeutic Activity Against Cognitive and Attention Deficits in Schizophrenia and ADHD, pp. 1-4, (2008). Presentation Abstract from Neuroscience 2008.
Pichat et al, SAR110894. A Novel, Potent and Selective H3-Receptor (H3-R) Antagonist II. Effects in Models Predictive of Therapeutic Activity Against Cognitive and Attention Deficits in Schizophrenia and ADHD, Poster 160.20/FF5, presented at the 38th Annual Meeting Society for Neuroscience (2008) (1 page).
Siemmelin. et al.. A Phase 2 Study to Investigate the Effects of SAR110894 on Cognition, Daily Function, Apathy, and Sleep in Mild to Moderate Alzheimer's Disease Patients, Abstract from 6th Conference Clinical Trials on Alzheimer's Disease, Journal of Nutrition, Health and Aging (2013) 17:9 (804-805) (2 pages).
ClinicalTrials.gov/archive—View of NCT01266525 on 2013_03_08, (2013), pp. 1-3. Retrieved from the Internet: URL: http://clinicaltrials.gov/archive/NCT01266525/2013_03_08 [retrieved on Feb. 3, 2014].
ClinicalTrials.gov/archive—View of NCT01266525 on 2015_01_22, (2015), (4 pages) Retrieved from the Internet: URL: http://clinicaltrials.gov/archive/NCT01266525/2015_01_22 [retrieved on Mar. 7, 2016].
International Search Report for International Application No. PCT/EP2014/069168, publication No. WO/2015/032966, created by the International Search Authority, mailed Nov. 26, 2014.
Sanofi.com—Summary results of DRI10734 (Nov. 11, 2014), (4 pages), Retrieved from the internet http://en.sanofi.com/img/content/study/DRI10734_summary.pdf [retrieved on Mar. 7. 2016].

* cited by examiner

FIG. 1

Mean ±sem
Non parametric statistical analysis (Kruskal-Wallis two-tailed comparisons *versus* Vehicule).

H3 RECEPTOR ANTAGONIST FOR USE IN THE TREATMENT OF ALZHEIMER'S DISEASE

This application is a continuation of U.S. application Ser. No. 14/506,089, filed Oct. 3, 2014, which is a continuation of International Application No. PCT/EP2013/057241, filed Apr. 5, 2013, which claims the benefit of priority of U.S. Provisional Application No. 61/792,635, filed Mar. 15, 2013, both of which are incorporated herein by reference, and which also claims priority to European Application No. 12305415.7, filed Apr. 6, 2012.

The present invention relates to the compound 2-(cyclohexylmethyl)-N-{2-[(2S)-1-methylpyrrolidin-2-yl]ethyl}-1,2,3,4-tetrahydroisoquinoline-7-sulfonamide for use in a disease modifying therapy for Alzheimer's disease (AD), other tauopathies and related neurodegenerative diseases.

BACKGROUND OF THE INVENTION

Tauopathies are a group of neurodegenerative diseases characterized by accumulation of tau (τ) protein in the brain. AD is the most prevalent of the tauopathies and the most common form of dementia. Other tauopathies and related neurodegenerative diseases include Pick's disease, progressive supranuclear palsy, corticobasal degeneration, hereditary fronto-temporal dementia and parkinsonism linked to chromosome 17 (FTDP-17).

Dementia is a brain disorder that seriously affects a person's ability to carry out normal daily activities. AD involves parts of the brain that control thought, memory, and language. Despite intensive research throughout the world, the causes of AD, except for rare reported cases of familial AD gene mutations, are still unknown and there is no cure.

There are several treatments for the cognitive symptoms of AD currently available. Of the five drugs currently being used in the United States for the treatment of AD, four of them are inhibitors of acetylcholinesterase. Another drug, memantine, an NMDA receptor antagonist, is available for treating moderate-to-severe AD. The drugs currently used for treating the cognitive symptoms of AD, including memantine and the acetylcholine esterase inhibitors, are marginally efficacious, and have not been shown to effectively slow or stop the progression of the disease. There is an increased interest in the development of therapies to impede the pathologic progression of AD because the pathophysiologic process leading to neurodegeneration in AD is thought to begin long before clinical symptoms develop. Thus, there is a large unmet need for drugs that may slow or stop the pathological progression of AD, and other tauopathies and neurodegenerative diseases.

The histamine H3 receptors are found in the central and peripheral nervous systems. The administration of histamine H3 receptor ligands may influence the secretion of neurotransmitters in the brain and the periphery and have been considered useful in the treatment of cognitive disorders, including AD and other dementias. Brioni et al. note that H3 antagonists could possibly be used for disease-modifying therapy in AD (*The Journal of Pharmacology and Experimental Therapeutics*, Vol. 336, No. 1, 38-46 (2011)).

The present invention is based on the novel result from preclinical studies that treatment with 2-(cyclohexylmethyl)-N-{2-[(2S)-1-methylpyrrolidin-2-yl]ethyl}-1,2,3,4-tetrahydroisoquinoline-7-sulfonamide can slow down the progression of tau pathology in a transgenic animal model at doses consistent with those used in the human population.

SUMMARY OF THE INVENTION

The present invention relates to methods of slowing or stopping the progression of AD and other tauopathies and related neurodegenerative diseases comprising administering to a patient in need thereof 2-(cyclohexylmethyl)-N-{2-[(2S)-1-methylpyrrolidin-2-yl]ethyl}-1,2,3,4-tetrahydroisoquinoline-7-sulfonamide or a pharmaceutically acceptable salt thereof.

Another aspect of the invention is the use of 2-(cyclohexylmethyl)-N-{2-[(2S)-1-methylpyrrolidin-2-yl]ethyl}-1,2,3,4-tetrahydroisoquinoline-7-sulfonamide or a pharmaceutically acceptable salt thereof to slow or stop the disease progression of AD and other tauopathies and related neurodegenerative diseases.

Another aspect of the invention is the compound 2-(cyclohexylmethyl)-N-{2-[(2S)-1-methylpyrrolidin-2-yl]ethyl}-1,2,3,4-tetrahydroisoquinoline-7-sulfonamide or a pharmaceutically acceptable salt thereof for use in slowing or stopping the disease progression of AD and other tauopathies and related neurodegenerative diseases.

DETAILED DESCRIPTION OF THE INVENTION

Definitions and Abbreviations

As used above, and throughout the description of the invention, the following abbreviations and symbols, unless otherwise indicated, shall be understood to have the following meanings:
AD Alzheimer's disease
ADAS Alzheimer's Disease Assessment Scale
BSA Bovine Serum Albumin
CSF Cerebrospinal fluid
DSM-IV Diagnostic and Statistical Manual of Mental Disorders (fourth edition)
MIP-1α Macrophage Inflammatory Protein 1-α
MRI Magnetic resonance imaging
NFTs Neurofibrillary tangles
PHF Paired helical filament
PBS Phosphate buffered saline
ROI Regions of interest
Tg Transgenic
WT Wild type
Veh Vehicle As used above, and throughout the description of the invention, the following terms, unless otherwise indicated, shall be understood to have the following meanings:

"Active Ingredient" as used herein, refers to 2-(cyclohexylmethyl)-N-{2-[(2S)-1-methylpyrrolidin-2-yl]ethyl}-1,2,3,4-tetrahydroisoquinoline-7-sulfonamide or a pharmaceutically acceptable salt thereof, a hydrate or solvate thereof, or a solvate or hydrate of a pharmaceutically acceptable salt.

"Impact on underlying disease" means an improvement in a measure of one or more biomarker or other parameter associated with the disease process, including, for example, a biochemical marker in CSF or plasma, a change in brain (or part of the brain) volume, a change in brain function as measured by functional imaging, changes in histopathology or biochemistry or a change on cognition or disability. Typical biomarkers that may be used for AD clinical trials and treatment include analytes measured in CSF, such as tau, phosphoTau, or beta-amyloid, for example.

"Patient in need of treatment" or "patient having a tauopathy or related neurodegenerative disease" as used herein includes patients 1) already diagnosed with a tauopathy, for example AD, or related neurodegenerative disease, at any clinical stage, including patients having mild cognitive impairment to advanced dementia; and/or 2) who has early or prodromal symptoms and signs of a tauopathy, for example AD, or related neurodegenerative disease; and/or 3) who has been diagnosed as susceptible to a tauopathy, for example AD, or related neurodegenerative disease, due to age, hereditary, a measurable biomarker, or other factors for whom a course of treatment is medically recommended to delay the onset or evolution or aggravation or deterioration of the symptoms or signs of disease.

"Patient" or "subject" includes any mammal. A "mammal", for purposes of treatment, refers to any animal classified as a mammal, including but not limited to humans, domestic and farm animals, and zoo, sports, or pet animals, such as dogs, horses, cats, cows, and the like. Preferably, the mammal is human.

As used herein, patients with "preclinical Alzheimer's disease" are those for whom the diagnosis is based on a measurable biomarker of Alzheimer's disease or the detection of subtle evidence of cognitive deficits, without functional impairment.

As used herein, patients with "mild cognitive impairment" are those for which a cognitive deficit is present, but without sufficient impairment to constitute dementia.

As used herein, patients with "mild to moderate Alzheimer's disease" are those for whom the diagnosis is based on Dementia of Alzheimer Type DSM-IV criteria and NINCDS/ADRDA criteria for Probable AD (National Institute of Neurological and Communicative Disorders and Stroke/AD and Related Disorders Association) with a Mini-MentalState Examination (MMSE) score ≥10 and ≤25 and a Cognitive Drug Research global score=0.5, 1, or 2.

As used herein, patients with "moderate to severe Alzheimer's disease" are those for whom the diagnosis is based on Dementia of Alzheimer Type DSM-IV criteria and NINCDS/ADRDA criteria for Probable AD (National Institute of Neurological and Communicative Disorders and Stroke/AD and Related Disorders Association) with a Mini-MentalState Examination (MMSE) score below 19 and a Cognitive Drug Research global score=2 or 3.

As used herein, the phrase "related neurodegenerative disease" includes, but is not limited to, Down's syndrome, myotonic dystrophy, and Niemann Pick type C disease.

The term "tauopathy" as used herein is any form of neurodegenerative disease that is associated with a tau pathology. AD and certain forms of fronto-temporal dementia (Pick's disease, sporadic fronto-temporal dementia and fronto-temporal dementia with Parkinsonism linked to chromosome 17) are the most common forms of tauopathy. Other tauopathies include, but are not limited to, progressive supranuclear palsy, dementia pugilistica (chronic traumatic encephalopathy), Lytico-Bodig disease (Parkinson-dementia complex of Guam), tangle-predominant dementia, argyrophilic grain disease, ganglioglioma and gangliocytoma, meningioangiomatosis, subacute sclerosing panencephalitis, lead encephalopathy, tuberous sclerosis, Hallervorden-Spatz disease and lipofuscinosis.

The terms "treating", "treatment", and the like are used herein to refer to obtaining a desired pharmacological and physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment", as used herein, covers any treatment of a disease in a mammal, particularly a human, and includes: (a) preventing the disease from occurring in a subject which may be predisposed to the disease but has not yet been diagnosed as having it, i.e., causing the clinical symptoms of the disease not to develop in a subject that may be predisposed to the disease but does not yet experience or display symptoms of the disease; (b) inhibiting the disease, i.e., arresting or reducing the development of the disease or its clinical symptoms; or (c) relieving the disease, i.e., causing regression of the disease and/or its symptoms or conditions.

As used herein, the wording "2-(cyclohexylmethyl)-N-{2-[(2S)-1-methylpyrrolidin-2-yl]ethyl}-1,2,3,4-tetrahydroisoquinoline-7-sulfonamide for use . . . " shall be understood as being equivalent to the wording "use of 2-(cyclohexylmethyl)-N-{2-[(2S)-1-methylpyrrolidin-2-yl]ethyl}-1,2,3,4-tetrahydroisoquinoline-7-sulfonamide for . . . " or "use of 2-(cyclohexylmethyl)-N-{2-[(2S)-1-methylpyrrolidin-2-yl]ethyl}-1,2,3,4-tetrahydroisoquinoline-7-sulfonamide for the preparation of a medicament for use in . . . ".

For purposes of the present invention, references to 2-(cyclohexylmethyl)-N-{2-[(2S)-1-methylpyrrolidin-2-yl]ethyl}-1,2,3,4-tetrahydroisoquinoline-7-sulfonamide include the pharmaceutically acceptable salts, hydrates and solvates thereof, and solvates and hydrates of the pharmaceutically acceptable salts. In one aspect, the 2-(cyclohexylmethyl)-N-{2-[(2S)-1-methylpyrrolidin-2-yl]ethyl}-1,2,3,4-tetrahydroisoquinoline-7-sulfonamide is 2-(cyclohexylmethyl)-N-{2-[(2S)-1-methylpyrrolidin-2-yl]ethyl}-1,2,3,4-tetrahydroisoquinoline-7-sulfonamide difumarate monohydrate.

2-(Cyclohexylmethyl)-N-{2-[(2S)-1-methylpyrrolidin-2-yl]ethyl}-1,2,3,4-tetrahydroisoquinoline-7-sulfonamide, which has the structure of Formula (I):

is a potent, specific non-imidazole histamine 3 (H3) receptor antagonist. A preparation and the physical properties and beneficial pharmacological properties of 2-(cyclohexylmethyl)-N-{2-[(2S)-1-methylpyrrolidin-2-yl]ethyl}-1,2,3,4-tetrahydroisoquinoline-7-sulfonamide are described in, for example, WO2005/118547 (also US2007/0105834). The difumarate monohydrate salt of 2-(cyclohexylmethyl)-N-{2-[(2S)-1-methylpyrrolidin-2-yl]ethyl}-1,2,3,4-tetrahydroisoquinoline-7-sulfonamide is described in WO2010/151611.

The tau protein is a microtubule-associated protein expressed in neurons. Tau protein hyperphosphorylation, formation of neurofibrillary tangles (NFTs) and neuroinflammation are pathological hallmarks of the brain in AD and other tauopathies (for example, Pick's disease, progressive supranuclear palsy, corticobasal degeneration, hereditary fronto-temporal dementia and parkinsonism linked to chromosome 17 (FTDP-17)), which accumulate or progress with the course of the diseases.

Inflammation is also a characteristic of AD. Increased occurrence of T cells has been reported in the brains of AD patients. Peripheral T cells of AD patients overexpress Macrophage Inflammatory Protein 1-α (MIP-1α), which binds to the chemokine receptor CCR5 on brain endothelial cells, and the MIP-1α-CCR5 interaction promotes T cells migrating through the endothelial tight junction into the brain. The up-regulation of CCR5 also plays a role in the recruitment and accumulation of microglia in senile plaques.

The THY-Tau22 transgenic mouse model was developed to study the role of tau protein in AD and other tauopathies. (See Schindowski et al., *The American Journal of Pathology*, Vol. 169, No. 2, pp. 599-616 (2006)). The THY-Tau22 mice show hyperphosphorylation of tau and neurofibrillary tangle-like inclusions (Gallyas positive). These mice also display memory deficits at 6 months of age. THY-Tau22 shows hyperphosphorylation of tau on several AD-relevant tau epitopes: AT8, AT100, AT180, AT270, 12E8, tau-pSer396, and AP422.

Applicants have now found that, at clinically relevant doses, 6 months of treatment with 2-(cyclohexylmethyl)-N-{2-[(2S)-1-methylpyrrolidin-2-yl]ethyl}-1,2,3,4-tetrahydroisoquinoline-7-sulfonamide difumarate monohydrate in THY-Tau22 transgenic mice model decreases hyperphosphorylation of tau, decreases the number of neurofibrillary tangles (NFTs), decreases neuroinflammation, and decreases cognitive deficits, which are pathological hallmarks of AD and other tauopathies and related neurodegenerative diseases.

The effect of the long duration of 2-(cyclohexylmethyl)-N-{2-[(2S)-1-methylpyrrolidin-2-yl]ethyl}-1,2,3,4-tetrahydroisoquinoline-7-sulfonamide difumarate monohydrate on these several pathological hallmarks of AD and tauopathies indicates that 2-(cyclohexylmethyl)-N-{2-[(2S)-1-methylpyrrolidin-2-yl]ethyl}-1,2,3,4-tetrahydroisoquinoline-7-sulfonamide could be used as a disease modifying agent in these diseases.

The lack of effect of short term administration (2-week, Example 2) of 2-(cyclohexylmethyl)-N-{2-[(2S)-1-methylpyrrolidin-2-yl]ethyl}-1,2,3,4-tetrahydroisoquinoline-7-sulfonamide difumarate monohydrate on tau phosphorylation, as measured by Western blot on AD-2 epitope in the hippocampus, is in contrast with the effect in histopathological studies of a 2-week treatment of a different H3 receptor antagonist, ABT-239, on protein tau hyperphosphorylation in the spinal cord and hippocampus of TAPP (tau×APP (β-amyloid precursor protein)) transgenic mice reported by Bitner et al. (*Neuropharmacology*, 60 (2011) pp. 460-466). This unexpected finding indicates that the effect of 2-(cyclohexylmethyl)-N-{2-[(2S)-1-methylpyrrolidin-2-yl]ethyl}-1,2,3,4-tetrahydroisoquinoline-7-sulfonamide has a different mechanism of action to the effect observed with ABT-239 and reported by Bitner (Id.).

The most material and direct way of demonstrating a disease-modifying effect of a treatment for AD would be to show that an important pathological feature of the disease has been modified. Since pathological evidence per se is available only through autopsy or brain biopsy, methods of more indirectly obtaining such evidence are necessary in a clinical setting. Methods of demonstrating the disease-modifying effects of drugs for AD, i.e., an impact on the underlying disease, include the use of clinical designs (e.g., randomized withdrawal study design, randomized start study design), biochemical markers (e.g., beta-amyloid peptides, tau protein), brain imaging outcome measures (e.g., volumetric magnetic resonance imaging, magnetic resonance spectroscopy, positron emission tomography, single-photon emission computerized tomography) and cognitive and disability measures.

One aspect of the invention is a method of inhibiting abnormal tau hyperphosphorylation or aggregation in a patient having a tauopathy or related neurodegenerative disease, comprising administering to said patient an effective amount of 2-(cyclohexylmethyl)-N-{2-[(2S)-1-methylpyrrolidin-2-yl]ethyl}-1,2,3,4-tetrahydroisoquinoline-7-sulfonamide or a pharmaceutically acceptable salt thereof.

Another aspect of the invention is the compound 2-(cyclohexylmethyl)-N-{2-[(2S)-1-methylpyrrolidin-2-yl]ethyl}-1,2,3,4-tetrahydroisoquinoline-7-sulfonamide or a pharmaceutically acceptable salt thereof for use in the prevention or the delay of the disease progression of a tauopathy or related neurodegenerative disease in a patient.

Another aspect of the invention is the compound 2-(cyclohexylmethyl)-N-{2-[(2S)-1-methylpyrrolidin-2-yl]ethyl}-1,2,3,4-tetrahydroisoquinoline-7-sulfonamide or one of its pharmaceutically acceptable salts for use in inhibiting abnormal tau hyperphosphorylation or aggregation in a patient having a tauopathy or related neurodegenerative disease.

Another aspect of the invention is a method of preventing or delaying the progression of a tauopathy or related neurodegenerative disease in a patient comprising administering 2-(cyclohexylmethyl)-N-{2-[(2S)-1-methylpyrrolidin-2-yl]ethyl}-1,2,3,4-tetrahydroisoquinoline-7-sulfonamide or a pharmaceutically acceptable salt thereof to said patient such that the progression of said tauopathy or neurodegenerative disease is delayed or prevented.

Another aspect of the invention is a method of reducing the level of phosphorylated tau protein in a patient having a tauopathy or related neurodegenerative disease, comprising administering to said patient 2-(cyclohexylmethyl)-N-{2-[(2S)-1-methylpyrrolidin-2-yl]ethyl}-1,2,3,4-tetrahydroisoquinoline-7-sulfonamide or a pharmaceutically acceptable salt thereof.

Another aspect of the invention is the compound 2-(cyclohexylmethyl)-N-{2-[(2S)-1-methylpyrrolidin-2-yl]ethyl}-1,2,3,4-tetrahydroisoquinoline-7-sulfonamide or one of its pharmaceutically acceptable salts for use in the reduction in the level of phosphorylated tau protein in a patient having a tauopathy or related neurodegenerative disease.

Another aspect of the invention is a method of inhibiting formation of neurofibrillary tangles in a patient with a tauopathy or related neurodegenerative disease, comprising administering 2-(cyclohexylmethyl)-N-{2-[(2S)-1-methylpyrrolidin-2-yl]ethyl}-1,2,3,4-tetrahydroisoquinoline-7-sulfonamide or a pharmaceutically acceptable salt thereof to said patient such that the formation of neurofibrillary tangles is inhibited.

Another aspect of the invention is the compound 2-(cyclohexylmethyl)-N-{2-[(2S)-1-methylpyrrolidin-2-yl]ethyl}-1,2,3,4-tetrahydroisoquinoline-7-sulfonamide or one of its pharmaceutically acceptable salts for use in inhibition of the formation of neurofibrillary tangles in a patient with a tauopathy or related neurodegenerative disease.

Another aspect of the invention is a method of treating a patient with a tauopathy or related neurodegenerative disease comprising administering to said patient 2-(cyclohexylmethyl)-N-{2-[(2S)-1-methylpyrrolidin-2-yl]ethyl}-1,2,3,4-tetrahydroisoquinoline-7-sulfonamide or a pharmaceutically acceptable salt thereof in an amount effective to inhibit the level and/or spreading of neurofibrillary tangles in neuronal cells in said patient.

Another aspect of the invention is the compound 2-(cyclohexylmethyl)-N-{2-[(2S)-1-methylpyrrolidin-2-yl]ethyl}-1,2,3,4-tetrahydroisoquinoline-7-sulfonamide or one of its pharmaceutically acceptable salts for use in the inhibition of the level and/or the spreading of neurofibrillary tangles in neuronal cells in a patient with a tauopathy or related neurodegenerative disease.

In a particular aspect, the level of phosphorylated tau and tau in the patient's cerebrospinal fluid is reduced.

Another aspect of the invention is a method of treating a patient with a tauopathy or related neurodegenerative disease comprising administering to said patient an amount of 2-(cyclohexylmethyl)-N-{2-[(2S)-1-methylpyrrolidin-2-yl]ethyl}-1,2,3,4-tetrahydroisoquinoline-7-sulfonamide, or one of its pharmaceutically acceptable salts, effective to decrease protein tau phosphorylation in said patient. In particular aspects of the invention, the tauopathy is Alzheimer's disease. In a more particular aspect, the treatment delays the transition from one stage of Alzheimer's disease to a more severe stage of Alzheimer's disease in said patient.

Another aspect of the invention is a method of modifying a tauopathy or related neurodegenerative disease in a patient, comprising administering to said patient an amount of 2-(cyclohexylmethyl)-N-{2-[(2S)-1-methylpyrrolidin-2-yl]ethyl}-1,2,3,4-tetrahydroisoquinoline-7-sulfonamide or one of its pharmaceutically acceptable salts which is therapeutically effective in slowing or stopping cytoskeleton dysfunction or perturbation of other tau-dependent functions.

Another aspect of the invention is a method of disrupting or causing the dissolution of tau aggregates in a patient with a tauopathy or related neurodegenerative disease, comprising administering to said patient a therapeutically effective amount of 2-(cyclohexylmethyl)-N-{2-[(2S)-1-methylpyrrolidin-2-yl]ethyl}-1,2,3,4-tetrahydroisoquinoline-7-sulfonamide or a pharmaceutically acceptable salt thereof.

Another aspect of the invention is the compound 2-(cyclohexylmethyl)-N-{2-[(2S)-1-methylpyrrolidin-2-yl]ethyl}-1,2,3,4-tetrahydroisoquinoline-7-sulfonamide or one of its pharmaceutically acceptable salts for use in disrupting or causing the dissolution of tau aggregates in a patient with a tauopathy or related neurodegenerative disease.

Another aspect of the invention is a method of treating a tauopathy or related neurodegenerative disease in a patient, comprising administering 2-(cyclohexylmethyl)-N-{2-[(2S)-1-methylpyrrolidin-2-yl]ethyl}-1,2,3,4-tetrahydroisoquinoline-7-sulfonamide or pharmaceutically acceptable salt thereof to the patient, wherein the 2-(cyclohexylmethyl)-N-{2-[(2S)-1-methylpyrrolidin-2-yl]ethyl}-1,2,3,4-tetrahydroisoquinoline-7-sulfonamide or pharmaceutically acceptable salt thereof is therapeutically effective in having an impact on the underlying disease.

Another aspect of the invention is a method of inhibiting or reducing phosphorylation of a tau protein in a neuron, glial cell or Lewy body, comprising exposing the neuron, glial cell or Lewy body to an effective amount of 2-(cyclohexylmethyl)-N-{2-[(2S)-1-methylpyrrolidin-2-yl]ethyl}-1,2,3,4-tetrahydroisoquinoline-7-sulfonamide or a pharmaceutically acceptable salt thereof. In a particular aspect, the tau protein is microtubule-associated tau protein. In another particular aspect, the tau protein is in a neurofibrillary tangle. In another aspect, the hyperphosphorylation of tau protein is inhibited or prevented.

Another aspect of the invention is a method of reducing the amount of tau protein and phosphorylation of tau in a cell comprising exposing the cell to an effective amount of 2-(cyclohexylmethyl)-N-{2-[(2S)-1-methylpyrrolidin-2-yl]ethyl}-1,2,3,4-tetrahydroisoquinoline-7-sulfonamide or a pharmaceutically acceptable salt thereof. In a particular aspect, the tau protein is abnormally phosphorylated. In another particular aspect, the abnormally phosphorylated tau protein is hyperphosphorylated.

In some embodiments of the invention, the tauopathy or related neurodegenerative disease is Alzheimer's disease.

In other embodiments of the invention, the tauopathy or related neurodegenerative disease is mild-to-moderate Alzheimer's disease.

In other embodiments of the invention, the tauopathy or related neurodegenerative disease is moderate-to-severe Alzheimer's disease.

In other embodiments of the invention, the tauopathy or related neurodegenerative disease is preclinical Alzheimer's disease.

In other embodiments of the invention, the tauopathy or related neurodegenerative disease is mild cognitive impairment.

In some embodiments of the invention, 2-(cyclohexylmethyl)-N-{2-[(2S)-1-methylpyrrolidin-2-yl]ethyl}-1,2,3,4-tetrahydroisoquinoline-7-sulfonamide or a pharmaceutically acceptable salt thereof is administered at least one time per day over a prolonged duration.

In one aspect, the treatment of AD further comprises the treatment of one or more symptoms of AD. For example, the treatment of AD comprises treatment of one or more symptoms selected from the group consisting of disturbances of memory, disturbances of praxis, disturbances of attention, confusion, irritability and aggression, mood swings, language breakdown, long-term memory loss, withdrawal of the sufferer, and loss of motor control.

In another aspect, the treatment of AD further comprises one or more factors selected from the group consisting of the maintenance or reduction of cognition (which can be measured by the ADAS-cognition subscale; maintenance or reduction of Activities of Daily Living (which can be measured by ADCS-ADL subscale); maintenance or reduction of the Mini Mental State Examination (MMSE) total score; maintenance or reduction of the five factors from the Cognitive Drug Research System (CDR-S) computerized assessment; maintenance or reduction of the Neuropsychiatric Inventory (NPI) score; maintenance or reduction of the NPI apathy score and in the Apathy Evaluation Scale-Informant (AES-I) score.

In some aspects of the invention, the administration of the Active Ingredient delays the transition from one stage of AD to a more severe stage of AD in a patient. For example, one embodiment of the invention includes the delay of the change of clinical dementia scale of one to two in a patient with AD. Another embodiment comprises the delay of the transition from mild-to-moderate AD to moderate to severe AD in a patient. Another embodiment comprises the delay of the transition from preclinical AD to mild cognitive impairment due to Alzheimer's disease. Another embodiment comprises the delay of the transition from mild cognitive impairment due to Alzheimer's disease to mild-to-moderate AD.

Modes of administration include, but are not limited to, oral, parenteral (e.g., subcutaneous, subdural, intravenous, intramuscular, intrathecal, intraperitoneal, intracerebral, intraarterial, or intralesional routes of administration), topical, localized (e.g., surgical application or surgical suppository), rectal, and pulmonary (e.g., aerosols, inhalation, or powder). The route of administration would be based on the composition being administered, tissue targeting, and the like, as would be known to the artisan of ordinary skill. The route of administration may be varied in any way, limited by the physical properties of the drugs and the convenience of the patient and the caregiver.

The Active Ingredient of the present invention is usually administered in the form of pharmaceutical compositions. The pharmaceutical compositions contain the Active Ingredient associated with one or more pharmaceutically acceptable carriers or excipients.

The excipients employed are typically ones suitable for administration to human subjects or other mammals. Pharmaceutically acceptable excipients include at least one component selected from the group comprising pharmaceutically acceptable carriers, diluents, coatings, adjuvants, excipients, or vehicles, such as preserving agents, fillers, disintegrating agents, wetting agents, emulsifying agents, stabilizing agents, suspending agents, isotonic agents, sweetening agents, flavoring agents, perfuming agents, coloring agents, antibacterial agents, antifungal agents, other therapeutic agents, lubricating agents, adsorption delaying or promoting agents, and dispensing agents, depending on the nature of the mode of administration and dosage forms.

The pharmaceutical compositions can be prepared using conventional techniques known to those skilled in the art.

In one aspect of the invention, the pharmaceutical compositions contain a therapeutically effective amount of the Active Ingredient. The term "therapeutically effective amount," as used herein, refers to an amount of the Active Ingredient present in the pharmaceutical composition being administered that is sufficient to elicit the desired pharmacological or therapeutic effect(s). In determining the effective amount or dose, a number of factors are considered by the attending clinician, including, but not limited to: the species of mammal, its size, age, and general health; the specific disease involved; the degree of involvement or the severity of the disease; the response of the individual patient; the mode of administration; the bioavailability characteristics of the preparation administered; the dose regimen selected; the use of concomitant medication; and other relevant circumstances.

In one aspect, the methods of the invention comprise administering to a patient about 0.25 to about 10 mg per day of 2-(cyclohexylmethyl)-N-{2-[(2S)-1-methylpyrrolidin-2-yl]ethyl}-1,2,3,4-tetrahydroisoquinoline-7-sulfonamide, or about 0.25 to about 10 mg per day of a pharmaceutically acceptable salt of 2-(cyclohexylmethyl)-N-{2-[(2S)-1-methylpyrrolidin-2-yl]ethyl}-1,2,3,4-tetrahydroisoquinoline-7-sulfonamide measured in base form. In particular embodiments, the methods of the invention comprise administering to the patient between about 0.5 mg to about 5 mg (for example, about 0.5, about 1 mg, about 1.5 mg, about 2 mg, about 2.5 mg, about 3 mg, about 3.5 mg, about 4 mg, about 4.5 mg, or about 5 mg) per day of 2-(cyclohexylmethyl)-N-{2-[(2S)-1-methylpyrrolidin-2-yl]ethyl}-1,2,3,4-tetrahydroisoquinoline-7-sulfonamide, or pharmaceutically acceptable salt thereof measured in base form. In another embodiment, the methods of the invention comprise administering to the patient between about 0.25 mg to about 2.5 mg per day of 2-(cyclohexylmethyl)-N-{2-[(2S)-1-methylpyrrolidin-2-yl]ethyl}-1,2,3,4-tetrahydroisoquinoline-7-sulfonamide, or pharmaceutically acceptable salt thereof measured in base form.

In some aspects of the invention, 2-(cyclohexylmethyl)-N-{2-[(2S)-1-methylpyrrolidin-2-yl]ethyl}-1,2,3,4-tetrahydroisoquinoline-7-sulfonamide is administered over a prolonged period, for example, for at least for six months. In another aspect, 2-(cyclohexylmethyl)-N-{2-[(2S)-1-methylpyrrolidin-2-yl]ethyl}-1,2,3,4-tetrahydroisoquinoline-7-sulfonamide is administered for a prolonged period selected from at least 3 months, at least 4 months, at least 5 months, at least 6 months, at least 7 months, at least 8 months, at least 9 months, at least 10 months, at least 11 months, and at least 12 months. In particular embodiments, 2-(cyclohexylmethyl)-N-{2-[(2S)-1-methylpyrrolidin-2-yl]ethyl}-1,2,3,4-tetrahydroisoquinoline-7-sulfonamide is administered at least one time per day over a prolonged period.

Another aspect of the invention is the use of 2-(cyclohexylmethyl)-N-{2-[(2S)-1-methylpyrrolidin-2-yl]ethyl}-1,2,3,4-tetrahydroisoquinoline-7-sulfonamide or a pharmaceutically acceptable salt thereof to slow or stop the disease progression of AD and other tauopathies and related neurodegenerative diseases. All of the aspects, embodiments, and features described above also apply to said use.

The following examples describe the effect of administration of 2-(cyclohexylmethyl)-N-{2-[(2S)-1-methylpyrrolidin-2-yl]ethyl}-1,2,3,4-tetrahydroisoquinoline-7-sulfonamide difumarate monohydrate in transgenic mice THY-Tau22 on:

protein tau hyperphosphorylation on AD-2 (pSer396-pSer404) epitope by Western blot analysis;

protein tau hyperphosphorylation on AT-8 (pSer199-202/Thr205) epitope, by immunohistochemistry, in cortex, hippocampus, and amygdala;

formation of NFTs in cortex, hippocampus, and amygdale by Gallyas staining; and neuroinflammation (mRNA expression of MIPα) in hippocampus, by quantitative real time polymerase chain reaction (QPCR).

Example 1

A single administration of 2-(cyclohexylmethyl)-N-{2-[(2S)-1-methylpyrrolidin-2-yl]ethyl}-1,2,3,4-tetrahydroisoquinoline-7-sulfonamide difumarate monohydrate (3 and 10 mg/kg per os (in suspension in methylcellulose/Tween 80)) in THY-Tau22 mice (9 mice per treatment group) did not elicit any effect on protein tau phosphorylation at AD-2 epitope in the cortex, by Western blot analysis.

Example 2

Two-week administration of 2-(cyclohexylmethyl)-N-{2-[(2S)-1-methylpyrrolidin-2-yl]ethyl}-1,2,3,4-tetrahydroisoquinoline-7-sulfonamide difumarate monohydrate (0.002% and 0.02% in drinking water) in THY-Tau22 mice (9 mice per treatment group) did not elicit any effect on protein tau phosphorylation at AD-2 epitope in the hippocampus, by Western blot analysis.

Exposures at the doses of 0.002% and 0.02% in water are in the same order of magnitude as the exposures at doses 0.0034% and 0.034% in food used in the study described in Example 3.

Example 3

2-(Cyclohexylmethyl)-N-{2-[(2S)-1-methylpyrrolidin-2-yl]ethyl}-1,2,3,4-tetrahydroisoquinoline-7-sulfonamide difumarate monohydrate was administered as a supplement in food at doses of 0.00034%, 0.0034% and 0.034% for six months in THY-Tau22 and wild type mice as follows:
Tg Veh (n=17)
Tg Active Ingredient—0.034% (n=17)
Tg Active Ingredient—0.0034% (n=17)
Tg Active Ingredient—0.00034% (n=17)
WT Veh (n=17)
WT Active Ingredient—0.034% (n=17)
WT Active Ingredient—0.0034% (n=17)
WT Active Ingredient—0.00034% (n=17)
WT groups treated with Active Ingredient are not used in the biochemical and histological studies.

Figure 2:
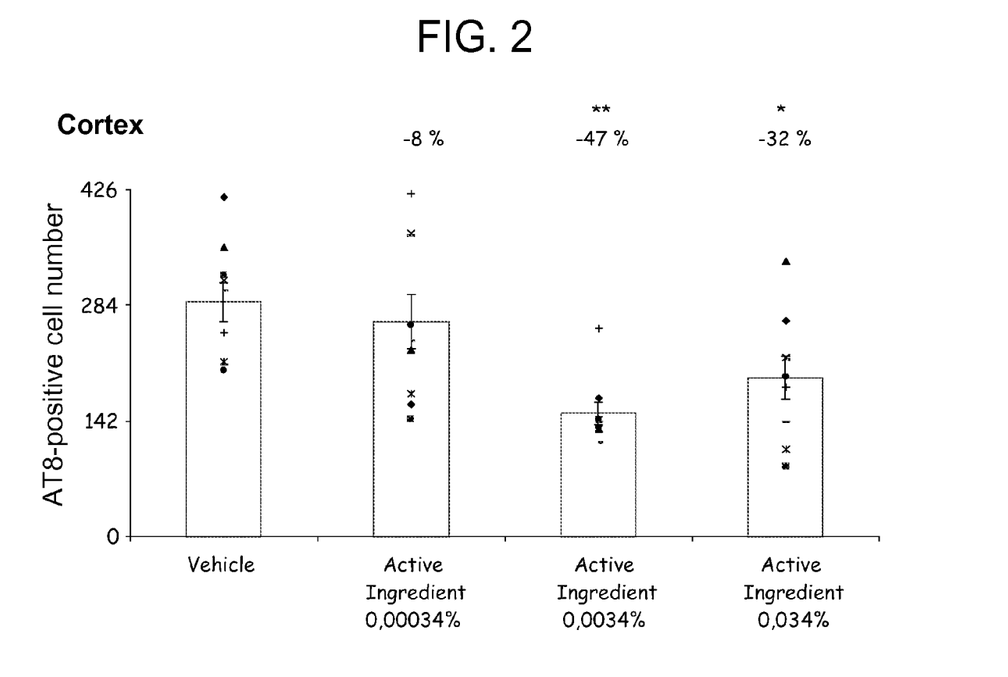
FIG. 2 illustrates the protective activity of the Active Ingredient in the cortex of THY-Tau22 mice against abnormal tau hyperphosphorylation (AT8 IHC) after 6 months treatment.
Figure 3:
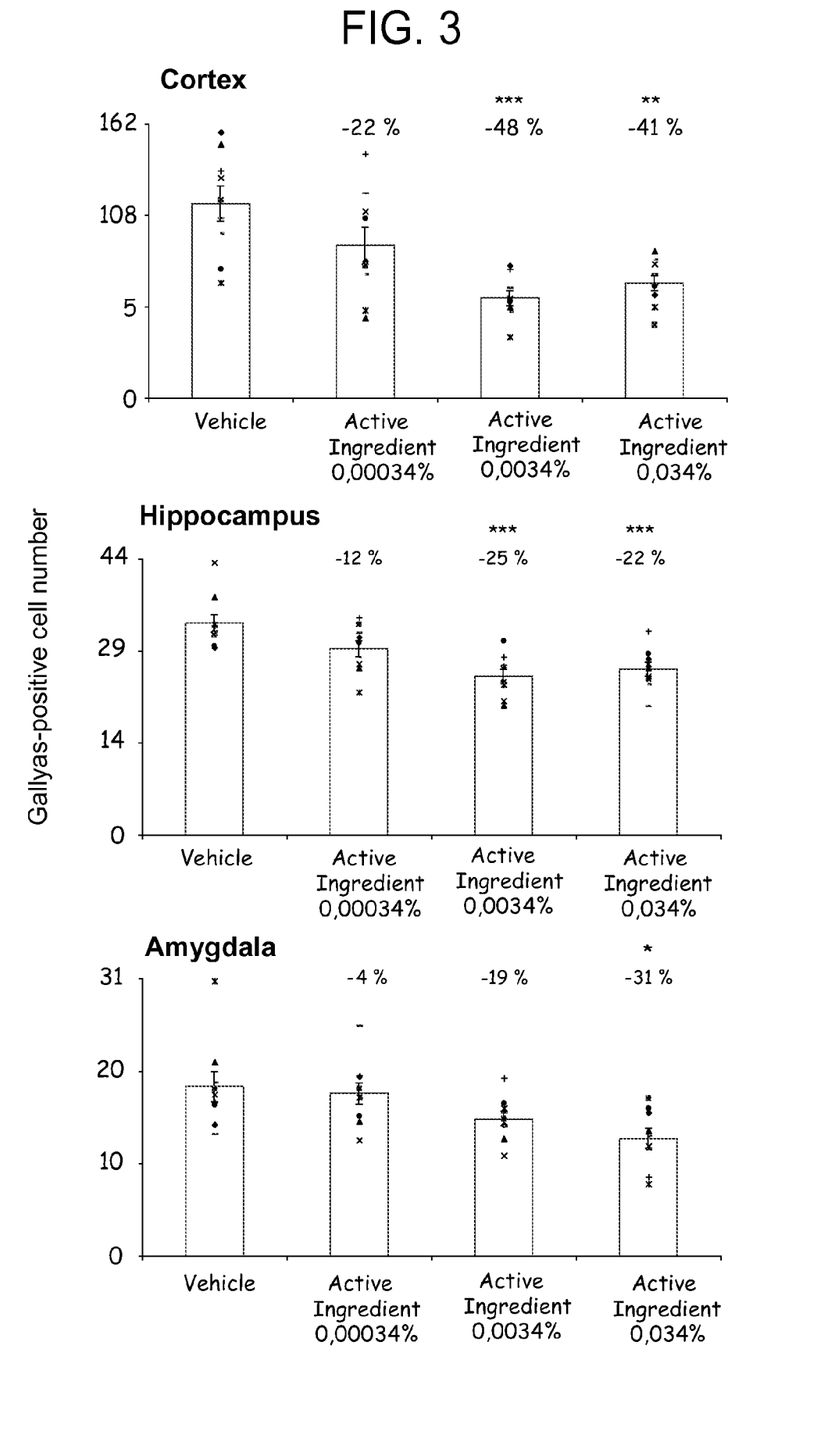
FIG. 3 illustrates the protective activity of the Active Ingredient in the cortex, CA1 hippocampal subarea, and amygdala of THY-Tau22 mice against NFTs formation (Gallyas staining) after 6 months treatment.
Figure 4:
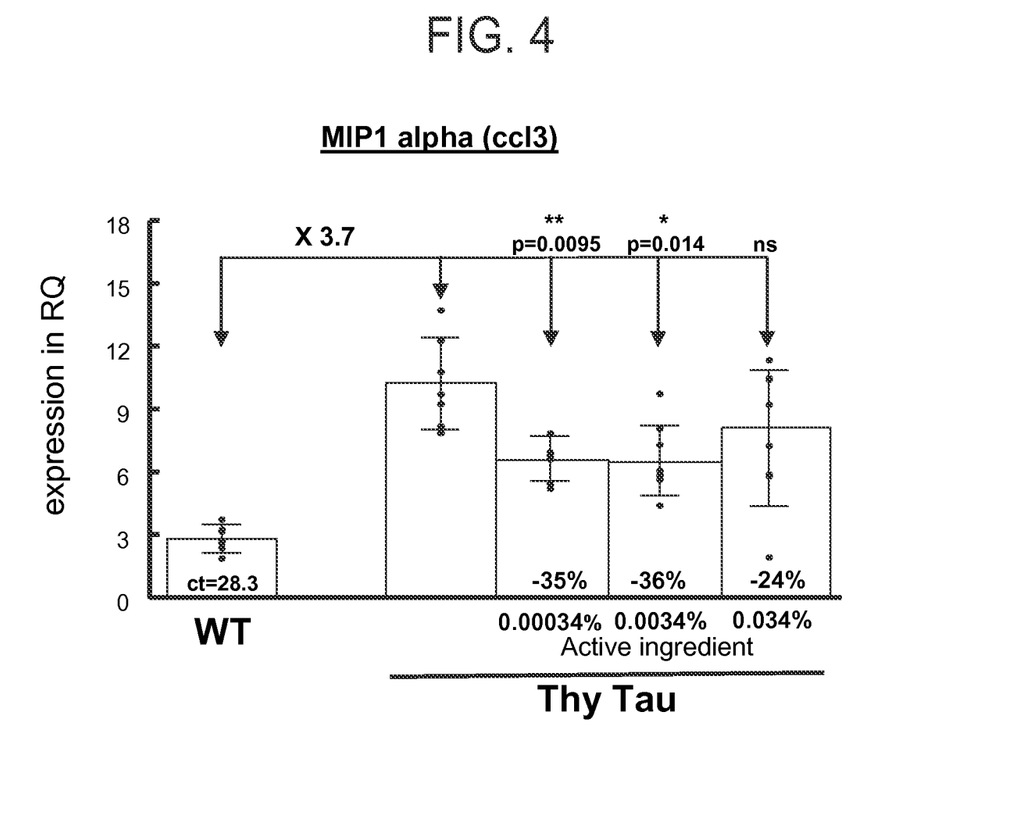
FIG. 4 illustrates the protective activity of Active Ingredient against MIP-1α gene over expression in the hippocampus of THY-Tau22 mice after 6 months treatment.

The following effects were observed compared to THY-Tau22 mice treated with vehicle (i.e., non-supplemented food):
statistical significant decrease of protein tau phosphorylation on AD-2 epitope in hippocampus at 0.0034% dosing (FIG. 1);
statistical significant decrease of protein tau phosphorylation on AT-8 epitope in cortex at 0.0034% and 0.034% dosings (n=9) (FIG. 2);
statistical significant decrease of NFTs formation in cortex, CA1 hippocampal subarea at 0.0034% and 0.034% dosings and in amygdala at 0.034% dosing (n=9) (FIG. 3);
statistical significant decrease of MIP-1α gene expression in hippocampus at 0.00034% and 0.0034% dosings (FIG. 4).

After 6 months of treatment with 2-(cyclohexylmethyl)-N-{2-[(2S)-1-methylpyrrolidin-2-yl]ethyl}-1,2,3,4-tetrahydroisoquinoline-7-sulfonamide difumarate monohydrate in THY-Tau22 transgenic mice, a significant decrease of the number of pathological neurons [i.e., neurofibrillary tangles (NFTs) evidenced by Gallyas silver impregnation] was observed in the cortex (−48% at 0.0034% and −41% at 0.034%). A significant decrease in the number of tangles was also observed in the CA1 hippocampal subarea (−25% at 0.0034% and −22% at 0.034%). Within the amygdala, the decrease in NFTs (−31%) was significant at the highest dose (0.034%) and a statistically non-significant decrease (−19%) at the 0.0034% dose. There was no protective effect against pathological neurons (i.e., tangles number) at the lowest dose (0.00034%) in all analyzed brain ROIs.

Within the cortex, a significant decrease of the number of AT8-positive neuronal cells (indicative of abnormal hyperphosphorylation of the protein TAU) was observed at the two highest doses (−47% at 0.0034% and −32% at 0.034%). In addition, a decrease in the intensity of AT8-immunostaining within neuronal cell bodies and fibers was qualitatively observed in the cortex of mice treated with the 0.0034% dose. No significant decrease of AT8-positive neuronal cell number was observed in other analysed ROIs (i.e., the amygdala and both CA1 and dentage gyrus hippocampal subareas).

Comparison of exposures achieved by the 6-month administration of 2-(cyclohexylmethyl)-N-{2-[(2S)-1-methylpyrrolidin-2-yl]ethyl}-1,2,3,4-tetrahydroisoquinoline-7-sulfonamide difumarate monohydrate administrations in the food of mice to those expected at steady state after 6-month oral administration in AD patients suggests that the 0.00034% and 0.0034% doses in mice correspond to doses which are safe for patients (about 0.25 and about 2.5 mg human dose, respectively).

Histopathological Analysis

Brain Tissue Sections

After mice were decapitated, brains were removed and one hemibrain (used for histopathological studies) was immersion-postfixed for seven days at 4° C. with 4% formaldehyde (Carlo Erba/code 415691). The other hemibrain was prepared for biochemical quantitative measurements.

Post-fixed hemibrains were incubated in phosphate-buffered saline (PBS, P 3813-10PAK, Sigma), transferred to a 20% sucrose solution (code 27480.294—Prolabo) for 48 hours at 4° C. to ensure good cryopreservation of tissues during subsequent freezing. For freezing, hemibrains were immersed for one minute in isopentane solution (Ref. No. 24872-323—Prolabo) cooled with dry ice to between −25° C. and −30° C. and then stored at −25° C.

The entire hemibrains were cut with a cryostat (Microm, HM560). Serial sagittal brain tissue sections were collected onto Superfrost plus microscope glass slides (VWR) and then stored at −20° C. (sections of 20 μm of thickness), or placed in PBS-sodium azide 0.1% (S-2002, Sigma) containing wells to avoid any contamination and stored at 4° C. (sections of 30 μm of thickness).

Gallyas Silver Staining

NFTs are a major defining neuropathological feature of tau pathology in AD. They consist of bundles of paired helical filaments and straight filaments and their main constituent is the hyperphosphorylated microtubule-associated protein tau. Gallyas staining is generally used to stain neurofibrillary pathology (Sun A. et al., *J. Histochem Cytochem*, 2002, 50, 4, pp. 463-472).

A series of 20 μm hemibrain sections (directly mounted on slides) per mice was used for Gallyas staining (Braak and Braak, 1991, *Brain Pathology*, 1, pp. 213-216). The detailed protocol is as follows:

The following reagents are used: periodic acid (Sigma Ref. No. P 7875); sodium hydroxide (Prolabo Ref. No. 1737-1000); potassium iodide (Merck Ref. No. 1.05043.1000); silver nitrate (Sigma Ref. No. S.8157); 100% ascetic acid (Prolabo Ref. No. 20 104.298); sodium carbonate, anhydrous (Merck Ref. No. 1.06392-0500); ammonium nitrate (Prolabo Ref. No. 21280-293); silicotungstic acid (Sigma Ref. No. T 2786); 40% formaldehyde (Carlo Erba Ref. No. 415661); sodium thiosulfate (Sigma Ref. No. 21724-500 g).

A first stock solution (No. 1) was prepared by dissolving 50 g of anhydrous sodium carbonate in 1000 ml of deionized water. A second stock solution (No. II) was prepared by dissolving 2 g of ammonium nitrate, 2 g of silver nitrate, and 10 g of silicotungstic acid in 1000 ml of deionized water. A third stock solution (No. III) was prepared by dissolving 2 g of ammonium nitrate, 2 g of silver nitrate, 10 g of silicotungstic acid, and 7.3 ml of commercial 37% formaldehyde solution in 1000 ml of deionized water. The stock solutions are stable and can be stored in opaque containers.

Each of the following steps in the method are carried out with stirring.
1. Pretreatment: The sections on slides were immersed in a solution of 5% periodic acid in water for 5 minutes, and then rinsed twice for 5 minutes in deionized water.

2. Argentation: The silver iodide solution is freshly prepared by dissolving 4 g of sodium hydroxide in 50 ml of distilled water and adding 10 g of potassium iodide, which is mixed and allowed to dissolve completely. 3.5 ml of a solution of 1% silver nitrate in water is added while stirring. Distilled water to a final volume of 100 ml is added, and the solution is mixed vigorously until clear. The hemibrain sections are immersed in the alkaline silver iodide solution for 1 minute. They are then rinsed in a solution of 0.5% acetic acid in water for approximately 10 minutes.
3. Detection: The detection agent is freshly prepared by mixing 10 volumes (50 ml) of stock solution I, 3 volumes (15 ml) of stock solution II, 7 volumes (35 ml) of stock solution III, which are mixed vigorously until the solution is clear. Detection takes from 5 to 30 minutes. If a pale brown color appears, detection is sufficient. The degree of detection is checked by observing the slides under the microscope.
4. The sections are rinsed rapidly in deionized water.
5. Fixation: The sections are fixed in 1% sodium thiosulfate for 5 minutes, and then rinsed rapidly in deionized water.
6. The sections are dehydrated on a hotplate.
7. A drop of mounting media (Pertex® Mounting Media) is placed on the slide and a coverslip is gently placed above.

Immunohistochemistry for AT8

Hyperphosphorylated microtubule-associated protein tau is the major component of the paired helical filament. Phosphorylation-dependent anti-tau antibodies can be used to identify specific amino acids that are phosphorylated in tau from normal brain and AD brain. For example, the monoclonal antibody, AT8, is widely used. Antibody that can detect the phosphorylated serine 202 and the phosphorylated threonine 205 epitopes of phosphorylated tau (AT8 epitope (M. Goedert et al., Neuroscience Letters, (1995) 189, 3, pp. 167-169)).

An immunohistochemical protocol using the AT8 antibody and based upon the avidin-biotin horseradish peroxidase method was applied on 30 μm free-floating sections. The detailed protocol is as follows:

The following reagents are used: 0.1M PBS buffer in 1 liter of $H_2O$ (2.23 g of $NaH_2PO4$, $2H_2O$ (Prolabo Ref. No. 33 616.262), 29 g of $Na_2HPO4$, 12 $H_2O$ (Prolabo Ref. No. 28 028.298), 9 g of NaCl (Prolabo Ref. No. 27 810.295)); PBS-Triton (0.15%) buffer Triton×100 (Sigma Ref. No. 23 479-9) (PBS-T) (1 l of 0.1M PBS buffer, 1.5 ml of Triton); 0.2M PBS buffer in 1 liter of $H_2O$ (4.46 g of $NaH_2PO4$, $2H_2O$, 58 g of $Na_2HPO4$, $12H_2O$, 18 g of NaCl); 30% $H_2O_2$ (Sigma Ref. No. H 1009); 3,3'-diaminobenzidine tetrahydrochloride (Sigma Ref. No. D9015, 100 mg stored at −20° C.); Vectastain® ABC Kit (Ref. No. PK 4000, Vector); BSA: bovine serum albumin (Sigma Ref. No. A8022).

Sections were preincubated for 3×10 minutes in 0.1 M-PBS-0.15% triton solution and then in 0.1M-PBS-1.5% hydrogen peroxide-50% methanol at room temperature for 30 minutes. After 3 washings in 0.1 M-PBS-0.15% triton, they were further incubated in blocking buffer [i.e., in BSA diluted at 10% in 0.01 M PBS] for 30 minutes. They were incubated at room temperature overnight with mouse anti-human PHF-Tau monoclonal antibody (clone AT8, Thermo Science, MN1020, dilution 1/500 in 0.1M PBS-0.05% Triton) and then with the secondary antibody (anti-mouse IgG biotinylated whole antibody from goat, Amersham, RPN1177, dilution 1/500 in 0.1M PBS-0.05% Triton) for 1 h 30. They were finally incubated in peroxidase-coupled avidin complex (Vectastain ABC kit, Vector Laboratories, dilution 1/400 in 0.1M PBS) for 30 minutes. Sections were briefly incubated in a peroxidase substrate solution (containing 0.003% hydrogen peroxide, 0.05% diaminobenzidine tetrahydrochloride in 0.1 M PBS) and rinsed in NaCl 0.9% solution. Finally, they were mounted on slides and dried at room temperature, dehydrated and coverslipped using Eukitt.

Quantitative Image Analysis of Gallyas Staining and AT8 Immunostaining

Two markers of tau pathology (i.e., Gallyas staining and AT8 immunostaining) were quantitatively determined using an image analysis system. Microscopic virtual slide technology (using an Olympus dotslide scanner system) was applied to acquire, at high magnification (i.e., objective ×10) and resolution, images of whole stained hemibrain sections. These sections were taken at different positions along the lateromedial axis of the different regions of interest (ROI).

All images were quantitatively analyzed on a computer-based workstation (Mercator system/Explora Nova using Dotslide software). The outlines of the different ROI were first defined manually for each image. For Gallyas staining, three ROI were analyzed: (cortex, CA1 subarea of the hippocampus, and amygdala). For AT8-immunostaining, four ROI were analyzed: cortex, amygdala, CA1 and dentate gyrus sub-areas of the hippocampus and dentate gyrus.

The total number of gallyas-positive or AT8-positive cells was estimated in the different ROI from 8 sections of the lateromedial axis of the hemibrain (in which tauopathy can be found in THY-TAU22 animals at the age of sacrifice, i.e. 8 months of age). This parameter was used to calculate the mean±SEM of the total number of Gallyas or AT8-positive cells in a given group.

All data were saved by the software and recovered by extraction in an Excel spreadsheet.

mRNA Expression of MIP1α—Protocol

1. RNA preparation: A hemi-hippocampus from each mouse was placed in a Precellys CK14 tube including 50 1.4 mm ceramic beads and 0.5 ml of Applied Biosystems nucleic acid purification lysis solution (1×). The tissue was homogenized using a homogenizer Precellys24 (Bertin technology) during 2×10 sec bursts. Total RNA was isolated using the 6100 PrepStation (Applied Biosystems), according to the manufacturer's instructions, including a DNase treatment (protocol Isolation of Total RNA from Plant and Animal Tissue). To assess the quality and concentration of the total RNA, 1 μl was analyzed on an RNA LabChip (Agilent) using a 2100 Bioanalyser, (Agilent Technologies).

2. Real Time PCR

2 μg of total RNA from each mouse was reverse transcribed with oligo (dT)16 and random primers using a High-Capacity cDNA Archive Kit (Applied Biosystems), following the manufacturer recommendations. The final reverse-transcription reaction included template was 100 μl. Samples were then incubated for 10 min at 25° C., followed by 120 min. at 37° C. and then heated at 95° C. to denature the enzymes and stop the reaction. For real time PCR, the housekeeping gene R.L37A, was amplified using a quantitect primer assay from Qiagen (QT00252266) and MIP1 alpha was amplified using the following primers (5'-TGC-CCTTGCTGTTCTTCTCT-3') SEQ ID NO: 1; (5'-GTG-GAATCTTCCGGCTGTAG-3') SEQ ID NO: 2. Amplification was performed according to the manufacturer instructions (Applied Biosystems), using an ABI Prism 7900 sequence detector.

3. Expression of Results

For qPCR, cycle threshold (Ct) values were converted in relative quantity (RQ) using the equation $2^{(Ct(L37a)-Ct(MIP1\ alpha))}$ for each hippocampus sample divided by $2^{(Ct(L37a)-Ct(MIP1\ alpha))}$ from a reference total brain sample.

Western Blot Analysis of Tau Phosphorylation on Cortex and Hippocampus Homogenates For immunoblot analysis, frozen mouse tissues (either hippocampus or cortex) were homogenized using a Precellys 24 tissue homogenizer in 350 µl RIPA buffer from Cell Signaling (20 mM Tris-HCl (pH 7.5), 150 mM NaCl, 1 mM Na$_2$ EDTA, 1 mM EGTA, 1% NP-40, 1% sodium deoxycholate, 2.5 mM sodium pyrophosphate, 1 mM beta-glycerophosphate, 1 mM Na$_3$VO$_4$, 1 µg/ml leupeptin) to which proteases inhibitors (Sigma cocktail 1% v/v) and phosphatases inhibitors (okadaic acid 1 µM, sodium fluoride 100 mM) were added. After centrifugation, 16000×g 4° C. for 10 minutes, protein content in supernatants was determined with BioRad DC Protein Assay kit, using BSA as a standard. Equal amounts of protein (5 µg) were loaded on 15-well 4-12% Bis-Tris gels (NuPAGE, Invitrogen) and electrophoresis was performed at 200V for 50 minutes in MOPS buffer according to the manufacturer's instructions. Proteins were then transferred to polyvinylidene difluoride (PVDF) membranes (Invitrogen) at 30 V for 2 hours in transfer buffer (Invitrogen) containing 20% methanol. After blocking in 5% non-fat dry milk in TBS Tween 0.1%, blots were incubated overnight at 4° C. in primary antibodies diluted in 5% BSA in TBS Tween 0.1%. Tau protein was detected using the following mouse antibody: AD-2 1/20.000$^e$ (Biorad, 56484) which recognizes tau protein phosphorylated on Ser396 and Ser404. Each blot was also re-probed with an anti β-actin antibody 1/5.000$^e$ (Sigma, A-5316) to normalise for total protein amount.

Following incubation with primary antibodies, blots were rinsed in TBS Tween 0.1% and incubated for 1 hour at room temperature in an anti-mouse IgG horseradish peroxidase (HRP)-linked secondary antibody 1/10,000$^e$ (GE healthcare, NA9310) diluted in 5% non-fat dry milk in TBS Tween 0.1%. After washing, blots were developed with enhanced chemiluminescence (ECL advance, GE Healthcare) and images were obtained using a luminescent image analyser LAS 3000 (FUJIFILM). Quantification of immunoreactive signal was performed using Multigauge V3.0 software (FUJIFILM). Each signal was normalized to β-actin (same gel, same well). For statistical analysis, a non-parametric test was used (Kruskal-Wallis two-tailed comparisons test versus Vehicle).

Figure 1:
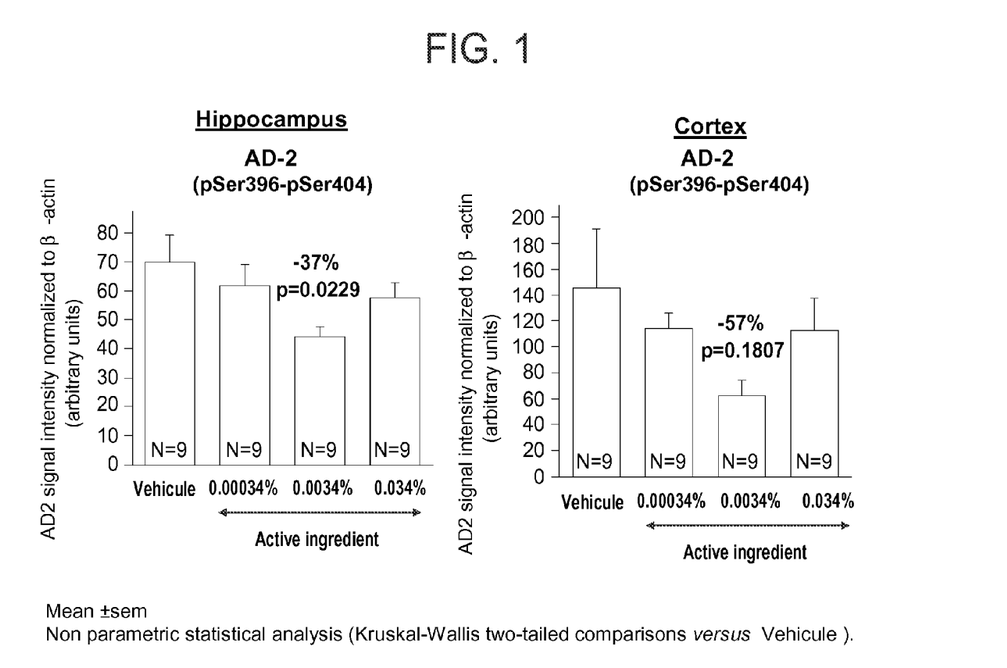
FIG. 1 illustrates the results of a Western blot analysis of tau phosphorylation on AD2 epitope (pSer396-pSer404) in the hippocampus (left) and cortex (right) of THY-Tau2 mice after 6 months of treatment with the Active Ingredient.

The inhibitory activity of the Active Ingredient in the hippocampus of THY-Tau22 mice against abnormal tau hyperphosphorylation is shown by Western blot analysis in FIG. 1.

There was a significant inhibition (−37%, p=0.0229) of tau phosphorylation at the AD-2 epitope at the dose of 0.0034%, but only a trend towards inhibition at the AT-8 epitope (−22%, ns). A similar but non-significant effect was also observed in the cortex (−57%, p=0.1807).

What is claimed is:

1. A method of delaying the disease progression of a tauopathy or related neurodegenerative disease, comprising administering to a patient in need thereof 2-(cyclohexylmethyl)-N-{2-[(2S)-1-methylpyrrolidin-2-yl]ethyl}-1,2,3,4-tetrahydroisoquinoline-7-sulfonamide or a pharmaceutically acceptable salt thereof; and wherein abnormal tau hyperphosphorylation or abnormal tau aggregation in said patient is thereby inhibited.

2. The method according to claim 1 in which the level of phosphorylated tau protein in said patient having a tauopathy or related neurodegenerative disease is reduced.

3. The method according to according to claim 1 in which formation of neurofibrillary tangles in said patient is inhibited.

4. The method according to according to claim 1 in which the level of neurofibrillary tangles in a neuronal cell in said patient is inhibited.

5. The method according to according to claim 1 in which cytoskeleton dysfunction or perturbation of other tau-dependent functions is slowed or stopped.

6. The method according to according to claim 1 in which the level of phosphorylated tau and tau in the patient's cerebrospinal fluid is reduced.

7. The method according to according to claim 1 in which tau aggregates in said patient are disrupted or dissolved.

8. The method according to according to claim 1 in which phosphorylation of tau protein in a neuron, glial cell or Lewy body in said patient is inhibited or reduced.

9. The method according to according to claim 8 in which the tau protein is microtubule-associated tau protein.

10. The method according to according to claim 9 in which the tau protein is in a neurofibrillary tangle.

11. The method according to according to claim 1 in which hyperphosphorylation of tau protein is inhibited or prevented.

12. The method according to according to claim 1 in which the tauopathy or related neurodegenerative disease is Alzheimer's disease.

13. The method according to according to claim 1 in which the tauopathy or related neurodegenerative disease is mild-to-moderate Alzheimer's disease.

14. The method according to according to claim 1 in which the tauopathy or related neurodegenerative disease is moderate-to-severe Alzheimer's disease.

15. The method according to according to claim 1 in which the tauopathy or related neurodegenerative disease is preclinical Alzheimer's disease.

16. The method according to according to claim 1 in which the tauopathy or related neurodegenerative disease is mild cognitive impairment.

17. The method according to according to claim 1 in which 2-(cyclohexylmethyl)-N-{2-[(2S)-1-methylpyrrolidin-2-yl]ethyl}-1,2,3,4-tetrahydroisoquinoline-7-sulfonamide or pharmaceutically acceptable salt thereof is administered at least one time a day for a prolonged duration.

18. The method according to according to claim 1 in which 2-(cyclohexylmethyl)-N-{2-[(2S)-1-methylpyrrolidin-2-yl]ethyl}-1,2,3,4-tetrahydroisoquinoline-7-sulfonamide or pharmaceutically acceptable salt thereof is 2-(cyclohexylmethyl)-N-{2-[(2S)-1-methylpyrrolidin-2-yl]ethyl}-1,2,3,4-tetrahydroisoquinoline-7-sulfonamide difumarate monohydrate.

19. The method according to according to claim 1 in which 2-(cyclohexylmethyl)-N-{2-[(2S)-1-methylpyrrolidin-2-yl]ethyl}-1,2,3,4-tetrahydroisoquinoline-7-sulfonamide or pharmaceutically acceptable salt thereof is to be administered at least one time per day over a prolonged period.

* * * * *

```
                        SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Primer for MIP1 alpha

<400> SEQUENCE: 1
tgcccttgct gttcttctct                                              20

<210> SEQ ID NO 2
<211> LENGTH: 20
<212> TYPE: DNA
<213> ORGANISM: Artificial Sequence
<220> FEATURE:
<223> OTHER INFORMATION: Primer for MIP1 alpha

<400> SEQUENCE: 2
gtggaatctt ccggctgtag                                              20
```